(12) United States Patent
Siemens

(10) Patent No.: US 9,964,486 B2
(45) Date of Patent: May 8, 2018

(54) ASSEMBLY FOR ATTENUATING IMPINGING LIGHT OF A BEAM OF RADIATION

(71) Applicant: AMRONA AG, Zug (CH)

(72) Inventor: Andreas Siemens, Laatzen (DE)

(73) Assignee: AMRONA AG, Zug (CH)

( * ) Notice: Subject to any disclaimer, the term of this patent is extended or adjusted under 35 U.S.C. 154(b) by 0 days. days.

(21) Appl. No.: 15/317,194

(22) PCT Filed: Mar. 25, 2015

(86) PCT No.: PCT/EP2015/056361
§ 371 (c)(1),
(2) Date: Dec. 8, 2016

(87) PCT Pub. No.: WO2016/000837
PCT Pub. Date: Jan. 7, 2016

(65) Prior Publication Data
US 2017/0153177 A1   Jun. 1, 2017

(30) Foreign Application Priority Data

Jul. 4, 2014   (EP) ..................................... 14175734

(51) Int. Cl.
*G01N 21/00* (2006.01)
*G01N 21/53* (2006.01)
(Continued)

(52) U.S. Cl.
CPC ........... *G01N 21/53* (2013.01); *G08B 17/107* (2013.01); *G08B 17/113* (2013.01);
(Continued)

(58) Field of Classification Search
CPC ............... G01N 21/53; G01N 15/0205; G01N 15/1459; G01N 21/51; G01N 15/1434
(Continued)

(56) References Cited

U.S. PATENT DOCUMENTS

| 8,390,806 B1 * | 3/2013 | Subramanian ........ G01J 3/0259 356/301 |
| 2003/0011770 A1 * | 1/2003 | Cole ...................... G01N 21/53 356/338 |

(Continued)

FOREIGN PATENT DOCUMENTS

| DE | 102005045280 B3 | 12/2006 |
| WO | 01/59737 A1 | 8/2001 |

*Primary Examiner* — Md M Rahman
(74) *Attorney, Agent, or Firm* — James D. Miller; Shumaker, Loop & Kendrick, LLP

(57) ABSTRACT

An assembly (100) for attenuating the impinging light of a beam of radiation of finite expansion with the objective of realizing reliable attenuation particularly of directly impinging light comprises a light source (10) for producing a beam of unpolarized light, preferably unpolarized monochromatic light, a useful light region (50) through which the unpolarized light passes and preferably passes through in a straight line from the light source (10) as well as an absorption device (30) arranged downstream of the useful light region (50) and preferably downstream in the direction of the direct beam radiation for at least partly absorbing impinging light, wherein the absorption device (30) comprises at least one polarization device (31, 32) arranged in the direction of the light beam.

17 Claims, 3 Drawing Sheets

(51) Int. Cl.
*G08B 17/107* (2006.01)
*G08B 17/113* (2006.01)
*G01N 21/47* (2006.01)

(52) U.S. Cl.
CPC . *G01N 2021/473* (2013.01); *G01N 2201/062* (2013.01); *G01N 2201/0642* (2013.01); *G01N 2201/0683* (2013.01)

(58) Field of Classification Search
USPC .......................................................... 356/338
See application file for complete search history.

(56) References Cited

U.S. PATENT DOCUMENTS

| | | | |
|---|---|---|---|
| 2004/0036775 A1* | 2/2004 | Watson, Jr. | G06T 5/50 348/207.1 |
| 2005/0063196 A1* | 3/2005 | Li | G02B 27/283 362/551 |
| 2005/0179904 A1 | 8/2005 | Larsen et al. | |
| 2005/0219536 A1* | 10/2005 | Feldman | G01J 9/00 356/419 |
| 2007/0021807 A1* | 1/2007 | Kurtz | A61N 5/0616 607/88 |
| 2007/0153122 A1* | 7/2007 | Ayite | H04N 13/0048 348/385.1 |
| 2009/0025453 A1* | 1/2009 | Griffith | G08B 17/10 73/31.02 |
| 2009/0046288 A1* | 2/2009 | Crafts | G01J 3/18 356/328 |
| 2010/0135619 A1* | 6/2010 | Choi | G02B 6/12007 385/88 |
| 2013/0101248 A1* | 4/2013 | Takasaka | G02B 6/2793 385/11 |
| 2015/0146146 A1* | 5/2015 | Lee | G02B 5/201 349/106 |
| 2016/0033328 A1* | 2/2016 | Walters | G01J 3/0264 356/327 |
| 2017/0153177 A1* | 6/2017 | Siemens | G01N 21/53 |

\* cited by examiner

ASSEMBLY FOR ATTENUATING IMPINGING LIGHT OF A BEAM OF RADIATION

CROSS-REFERENCES TO RELATED APPLICATIONS

This patent application is a United States national phase patent application based on PCT/EP2015/056361 filed on Mar. 25, 2015, which claims the benefit of European Patent Application No. 20140175734 filed on Jul. 4, 2014. The entire disclosures of the above patent applications are hereby incorporated herein by reference.

FIELD OF THE INVENTION

The present invention relates to an assembly for attenuating impinging light of a beam of radiation.

BACKGROUND

In certain technical equipment such as, for example, scattered-light smoke detectors, light is selectively introduced into a useful light region, for example a scattered light region, and any reflections there may be are detected by means of one or more optical detectors such as, for example, photodiodes and the like. In scattered-light smoke detectors, almost monochromatic light or infrared radiation of a laser or light-emitting diode generally propagates in a straight line from the light source into the useful light region. When scattered there by any smoke or similar particle there may be, a lesser amount of this scattered (reflected, as the case may be) light strikes the optical detectors arranged around the useful light region, whereby a signal is produced in same. Depending on the application, different signal processing methods are thereby used; should certain conditions be fulfilled, this type of scattered-light smoke detector can emit a warning signal or the like.

Of great importance in such applications is for structural measures to ensure that apart from the scattered light, which is actually scattered and/or reflected on the particles to be detected within the useful light region, as little stray light as possible reaches the optical detectors. Stray light is light which is for example reflected by the inner walls, etc. of the scattered-light smoke detector. When too much stray light strikes the optical detectors, the optical detectors produce too high of a background signal such that the stray light barely stands out from the background signal and is therefore difficult or impossible to detect. Particularly in the case of highly sensitive scattered-light smoke detectors, it becomes necessary to greatly amplify the scattered-light signals, which would lead to overmodulation of the amplifier at high background signals.

Light traps are known for the purpose of attenuating or absorbing unwanted light. For example, printed publication DE 10 2005 045 280 B3 discloses an optical distance sensor having such a light trap, whereby the light trap is arranged in the direct proximity of the light source in order to absorb the scattered light which propagates directly from the light source in a different direction than the nominal direction of the beam to be emitted. This conventional light trap is of relatively complicated structure, whereby incoming beams of light are reflected by the light trap such that they die out and are no longer routed out of the light trap. To this end, the conventional light trap provides for scored surfaces or folding within the light trap.

The light trap known from DE 10 2005 045 280 B3 thus has a relatively complicated structure for the purpose of effectively absorbing impinging light. The conventional light trap is moreover arranged to the side of a photo-optical receiver and thereby only serves to attenuate light reflected onto said receiver; i.e. on its surface. Therefore, in the case of an arrangement as found in a scattered-light smoke detector or the like and in which the beam of light (beam) emitted by the light source is not conducted directly onto a receiver element, this conventional light trap is not suited to sufficiently absorbing the directly impinging and relatively strong beam of light and thus preventing it from reflecting back into the useful light region.

SUMMARY OF THE INVENTION

Given this problem as set forth, the present invention is based on the task of specifying an assembly for attenuating impinging light of a beam of finite expansion which has a comparatively simple structure and which is able to absorb (so as attenuate) directly impinging light of a light source such as for example a laser light source or the like.

This task is solved according to the invention by an assembly for attenuating impinging light of a beam of finite expansion having the features of independent claim 1.

The task is in particular solved by an assembly for attenuating impinging light of a beam of finite expansion, preferably directly impinging monochromatic light, wherein the assembly comprises a light source for generating a beam of unpolarized light, preferably unpolarized monochromatic light, a useful light region through which the unpolarized light passes, and preferably passes through in a straight line from the light source, as well as an absorption device arranged downstream of the useful light region, and preferably downstream in the direct beam radiation direction, for at least partially absorbing impinging light, wherein the absorption device has at least one polarization device arranged in the direction of the light beam.

Making use of at least one polarization device makes reliable attenuating of the directly impinging light after it passes unpolarized through the useful light region surprisingly easy. Because polarizing devices are available at low cost, there is thus a simple economically advantageous way to effectively minimize the background signal which stray light produces in devices making use of this type of assembly. This particularly applies to the case in which the absorption device is arranged downstream of the useful light region in the direction of the direct beam radiation; thus, in other words, impinged by the full, relatively strong beam, which originates for example from a monochromatic laser light source or from an almost monochromatic LED light source.

Advantageous further developments of the inventive solution are set forth in the dependent claims.

It is thus for example provided for at least one optical detector for detecting scattered light to be arranged around the useful light region. Therefore, when not only is the impinging of scattered light, which negatively impacts the useful light region, to be prevented but optical detection is also to occur very selectively about said useful light region, then better optical detection accuracy can be achieved with the inventive assembly, which further reduces the background signal due to scattered light unwantedly being scattered back into the useful light region.

According to a further aspect of the invention, it is provided for the absorption device to have at least two polarization devices arranged in succession in the direction of the light beam. The successive arrangement of at least two polarization devices for absorbing the impinging beam of light surprisingly proves to be able to even further improve the absorptive properties significantly.

Tied in with this further development, it is for example provided for the at least two polarization devices to comprise a first linear polarizing filter and a second linear polarizing filter. The polarizing directions of the first and second linear polarizing filters are thereby offset 90° relative to each other. Turning the polarizing planes of the two linear polarizing filters arranged in succession in the direction of the light beam in this way further improves the absorptive effect.

It is alternatively possible in conjunction with the above-cited further development for the at least two polarization devices to have a first circular polarizing filter and a second circular polarizing filter. The polarizing direction of rotation of the first polarizing filter in the direction of the incident beam of light is thereby the same as the polarizing direction of rotation of the second polarizing filter in the direction of the incident beam of light. In other words: The two circular polarizing filters arranged successively in the direction of the light beam are not rotated in opposite directions to each other. Compared to the successively arranged linear polarizing filters, this further development of the invention can achieve further improving an excellent absorptive effect.

It is however likewise possible for the polarizing direction of the first circular polarizing filter to also be offset 90° from that of the second circular polarizing filter.

A linear polarizing filter can additionally be provided in the further developments comprising the circular polarizing filters, same being allocated to the at least one optical detector. In other words: A linear polarizing filter is arranged directly ahead of the at least one optical detector while the two circular polarizing filters having the same direction of rotation are directly arranged in succession in the direction of the beam and attenuate said beam after it crosses the useful light region. Doing so can thereby further reduce the background signal produced by stray light on the at least one optical detector.

According to one further aspect of the inventive solution, it is provided for the at least one polarization device to be exchangeably accommodated in a retaining device arranged downstream the useful light region in the direction of the beam. This facilitates and simplifies handling of the absorption device, for example when polarization device(s) is/are to be replaced. This type of mounting furthermore enables easy retrofitting of existing apparatus which are to make use of the inventive assembly.

According to a further aspect of the inventive solution, it is provided for the light source to comprise a light-emitting diode and preferably at least one lens as well as preferably at least one aperture. Such an optical system is of relatively simple and thus economical manufacture and at the same time allows for selectively impinging the useful light region with the light or infrared or ultraviolet radiation to be utilized.

According to a further aspect of the inventive solution, it is provided for the at least one optical detector to comprise a photodiode and preferably at least one lens as well as preferably at least one aperture. Also equally applicable to this optical system is it being able to be provided relatively economically and at the same time having high detection accuracy.

According to a further aspect of the invention, it is provided for the at least two polarization devices to be spaced apart from one another in the direction of the beam of light at a distance of less than 5 mm, and preferably less than 2 mm. The relatively small spacing of the two polarization devices from each other in the direction of the beam can further improve the absorption capacity.

According to one further aspect of the invention, it is provided for the at least one polarization device to be inclined at an angle relative to the direction of the incident beam of light, wherein the angle is formed between the incident beam of light and a detection plane within which the central optical axis of the at least one detector is arranged, and wherein the angle is preferably approximately 45°. In other words: The at least one polarization device and the preferentially at least two polarization devices are tilted together relative to the incident beam of light so that any incident light there may be which is not absorbed by the absorption device or is insufficiently attenuated is not reflected back the same way it arrived. When the assembly is used in a scattered-light smoke detector, the tilting can then instead reflect it to the bottom of the scattered-light smoke detector. The efficiency of the assembly is thereby increased to the effect of being able to even better prevent unwanted scattered light in the useful light region.

The invention is also directed toward a scattered-light smoke detector having at least one supply opening for supplying ambient air and an inventive assembly as described above, wherein the supply opening empties into a scattered light region, and wherein at least part of the scattered light region coincides with the useful light region.

BRIEF DESCRIPTION OF THE DRAWINGS

The following will reference the drawings in describing an embodiment of the inventive assembly for attenuating impinging light of a beam of finite expansion in greater detail. The drawings show.

DETAILED DESCRIPTION OF THE INVENTION

Figure 1:
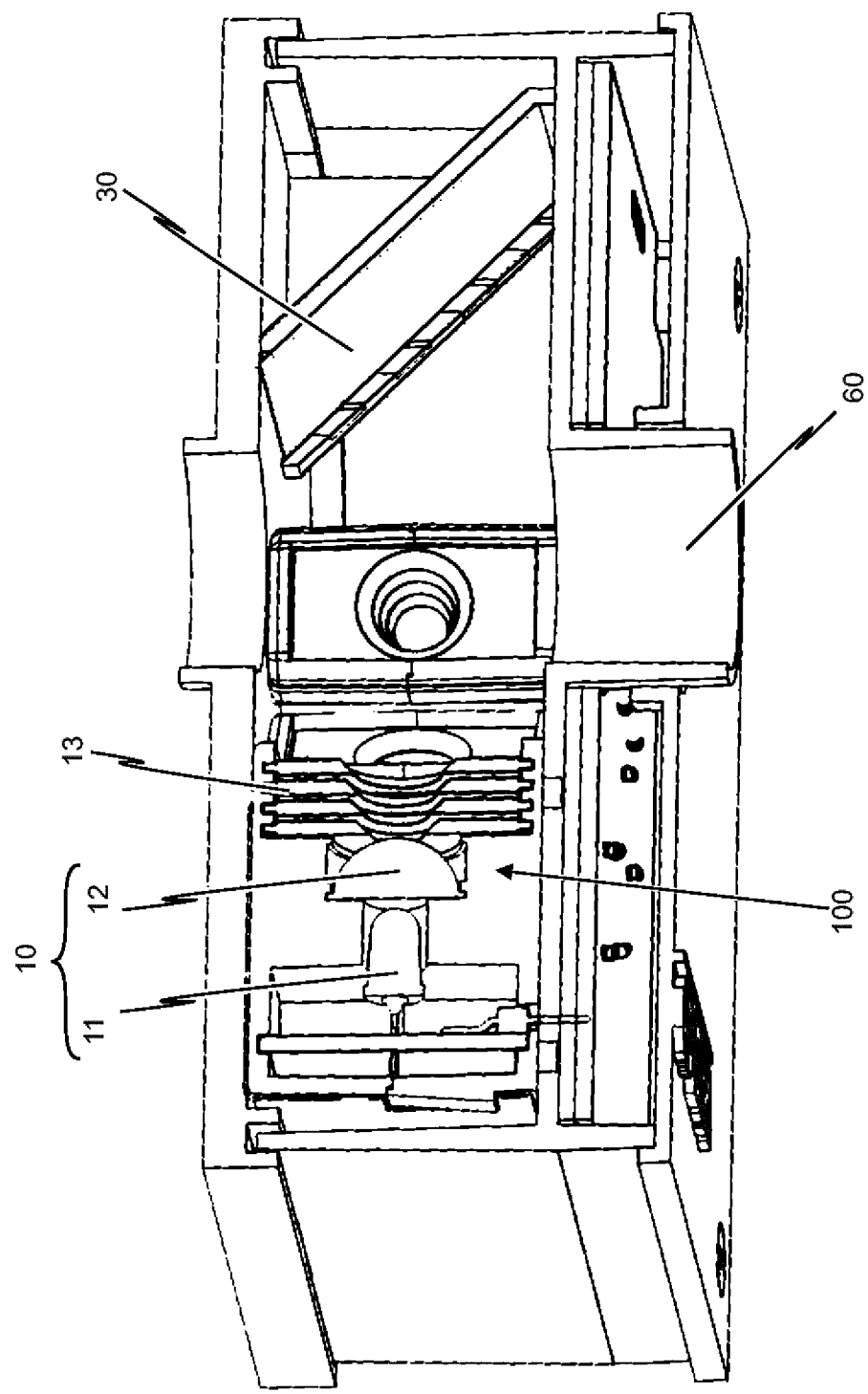
FIG. 1: a perspective sectional view of an inventive assembly for attenuating impinging light in accordance with one embodiment of the invention.

FIG. 1 shows a perspective sectional view of an inventive assembly 100 for attenuating impinging light of a beam of finite expansion in accordance with one embodiment of the invention. The assembly 100 is hereby used by way of example in a scattered-light smoke detector which has a supply opening 60 in its lower region for supplying ambient air into a useful light region 50 (not further identified in FIG. 1). Within the otherwise lightproof housing of the scattered-light smoke detector depicted in FIG. 1, a light source, identified as a whole by reference numeral 10, is provided ahead of the useful light region 50 for the purpose of impinging it with light. The light source comprises a light-emitting diode 11 and a lens 12 downstream of the light-emitting diode 11, with a plurality of apertures 13 being in turn arranged downstream thereof which focus all the light emitted by the light-emitting diode 11 and feed it into the useful light region. The unpolarized light passes through the useful light region 50; in a straight line in the embodiment depicted in FIG. 1. An absorption device 30 is arranged downstream of the useful light region 50 in the direct beam radiation direction which serves to absorb at least part of the impinging light. In the embodiment depicted, the absorption device 30 comprises two circular polarization devices 31, 32 arranged in succession, their polarizing direction of rotation being the same.

Figure 2:
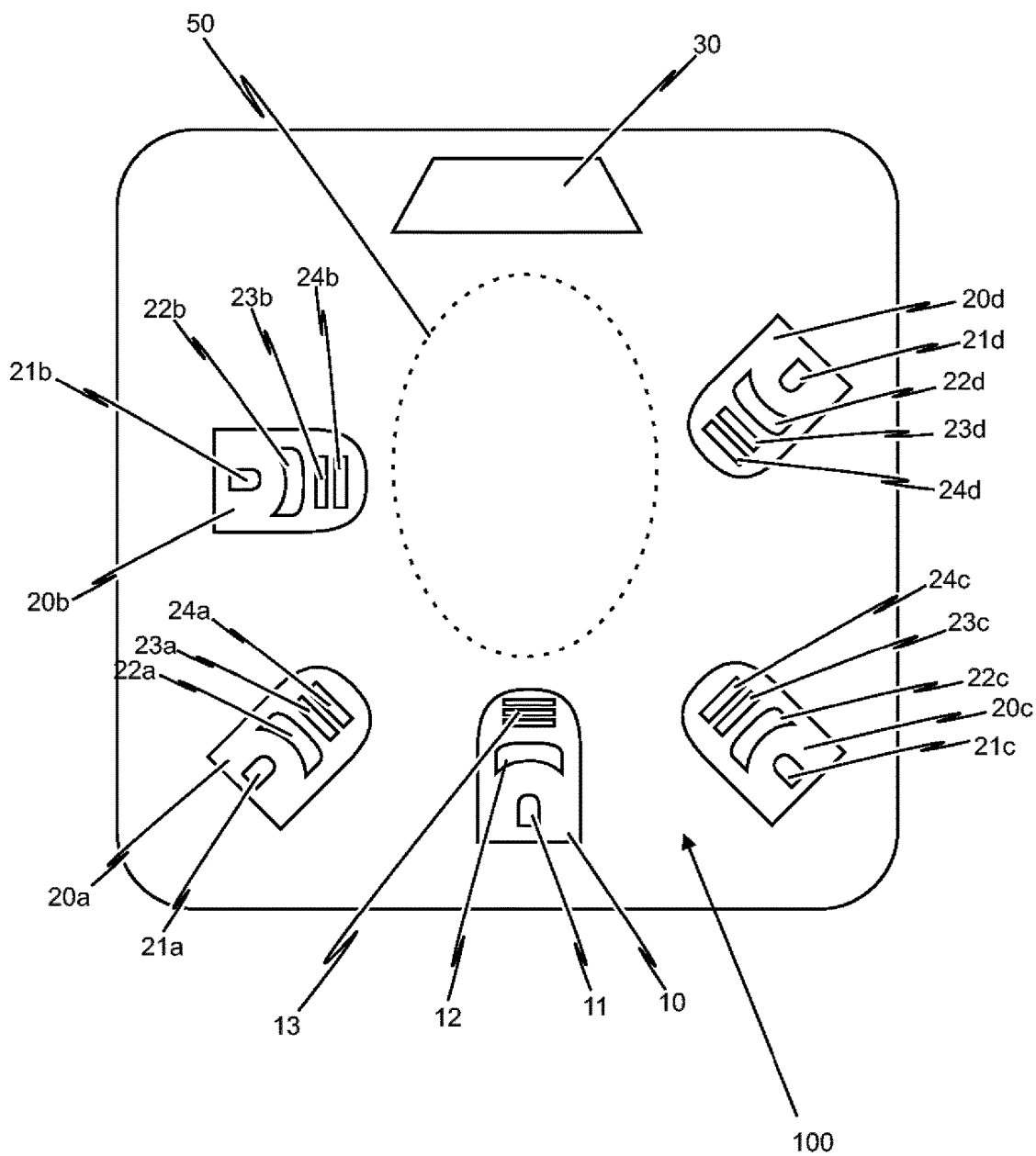
FIG. 2: a schematic plan view of the assembly of FIG. 1.

As is more readily visible from the schematic plan view of FIG. 2, a plurality of optical detectors 20a, 20b, 20c, 20d are arranged around the useful light region 50, indicated in the figure by dots, which serves in classifying any scattered light signal potentially detected in the assembly 100. The optical detectors 20a, 20b, 20c, 20d comprise a photodiode 21a, 21b, 21c, 21d and a lens 22a, 22b, 22c, 22d downstream of said photodiode 21a, 21b, 21c, 21d, downstream of which is in turn one or more apertures 23a, 23b, 23c, 23d, each of which is associated with a horizontally or vertically aligned linear polarization device 24a, 24b, 24c, 24d, for example a linear polarizing filter.

Figure 3:
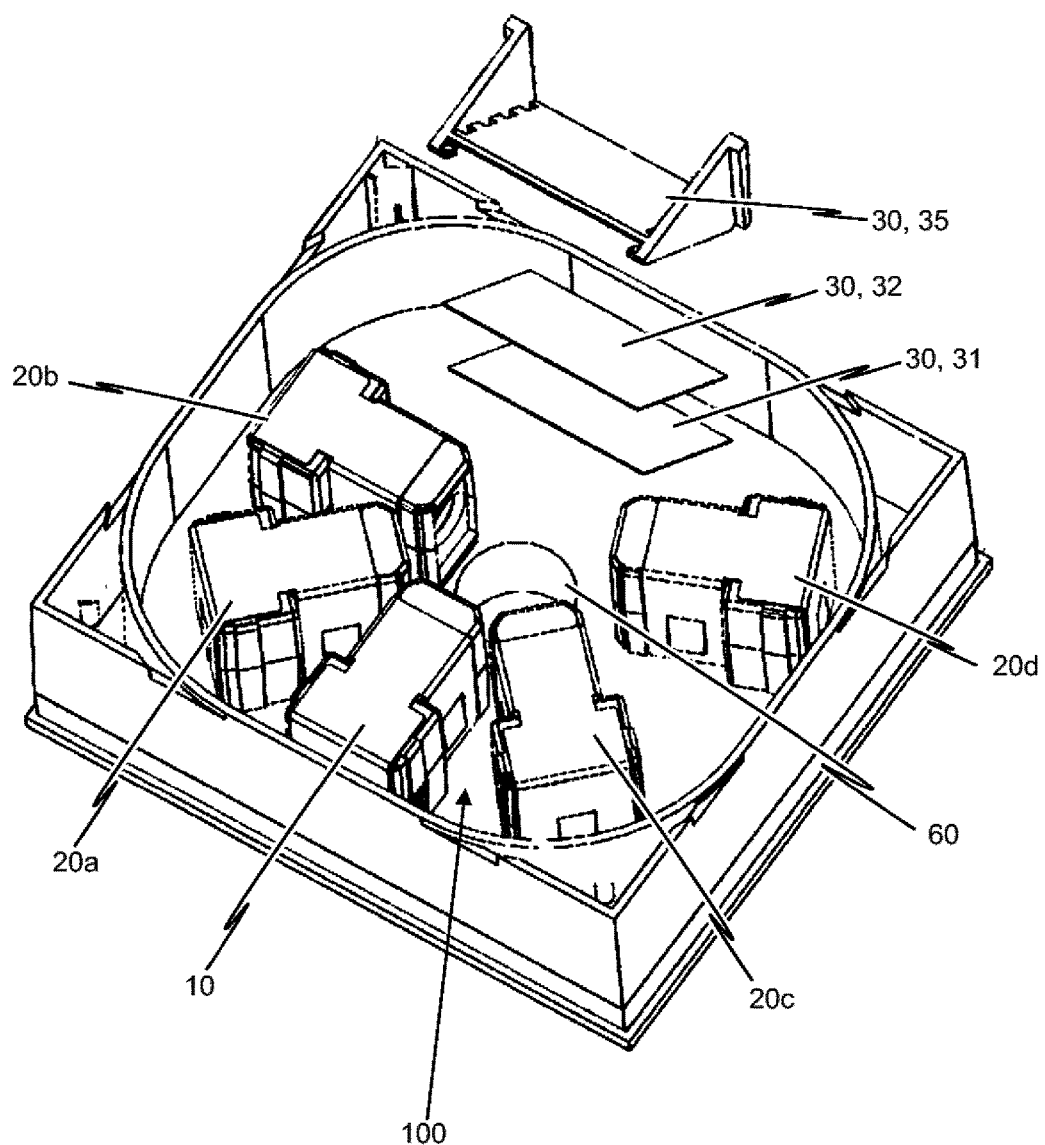
FIG. 3: a perspective plan view of the assembly of FIGS. 1 and 2, wherein the absorption device thereof is shown in exploded view for better visualization.

As is more readily visible from the perspective plan view of FIG. 3, the absorption device 30, depicted in the figure in exploded view for better visualization, comprises a retaining device 35, which in the mounted state has a mounting surface angled approximately 45° toward the bottom of the scattered-light smoke detector opposite from the beam of light emitted by the light source. The circular polarization devices 31, 32 are arranged successively on said mounting surface very close to one another, at a spacing of 2 mm apart in the depicted embodiment, which very effectively attenuates the directly impinging monochromatic light of the light-emitting diode 11 focused by the lens 12 and directed by the apertures 13 into the useful light region 50 so that its intensity is sufficiently low enough to not be undesirably detected by the optical detectors 20a, 20b, 20c, 20d as a result of interreflection or the like.

It is understood that the embodiment as depicted only serves enhanced illustrative purposes and is not to be regarded as limiting. Additions to and modifications of the inventive concept will be familiar to one skilled in the art.

LIST OF REFERENCE NUMERALS 10 light source
11 light-emitting diode
12 lens
13 aperture
20a, 20b, 20c, 20d optical detector
21a, 21b, 21c, 21d photodiode
22a, 22b, 22c, 22d lens
23a, 23b, 23c, 23d aperture
24a, 24b, 24c, 24d linear polarizing filter
30 absorption device
31 first polarization device
32 second polarization device
35 retaining device
50 useful light region
60 supply opening
100 assembly for attenuating impinging light

The invention claimed is:

1. An assembly for attenuating impinging light of a beam of finite expansion, preferably directly impinging monochromatic light, wherein the assembly comprises the following:
   a light source (10) for producing a beam of unpolarized light, preferably unpolarized monochromatic light;
   a useful light region (50) through which the unpolarized light passes, and preferably passes through in a straight line from the light source (10);
   an absorption device (30) arranged downstream of the useful light region (50) in the direction of the beam of unpolarized light for at least partly absorbing impinging light, wherein the absorption device (30) comprises at least one polarization device (31, 32) arranged in the direction of the beam of unpolarized light, and wherein at least one optical detector (20a, 20b, 20c, 20d) is arranged around the useful light region (50) for detecting scattered light, wherein the at least one polarization device (31, 32) is slanted at an angle relative to the direction of the impinging beam of unpolarized light, wherein the angle is formed between the impinging beam of unpolarized light and a detection plane within which a central optical axis of the least one detector (20a, 20b, 20c, 20d) is arranged, and wherein the angle preferably amounts to approximately 45°.

2. The assembly (100) according to claim 1, wherein the at least one optical detector comprises a photodiode and preferably at least one lens and preferably at least one aperture.

3. The assembly (100) according to claim 1, wherein the absorption device (30) comprises at least two polarization devices (31, 32) arranged successively in the direction of the beam of unpolarized light.

4. The assembly (100) according to claim 3, wherein the at least two polarization devices (31, 32) comprise a first linear polarizing filter and a second linear polarizing filter, wherein the polarizing directions of the first and second linear polarizing filter are offset 90° from one another.

5. The assembly (100) according to claim 4, wherein the at least one optical detector (20a, 20b, 20c, 20d) is assigned to a linear polarizing filter (21a, 21b, 21c, 21d).

6. The assembly (100) according to claim 3, wherein the at least two polarization devices (31, 32) comprise a first circular polarizing filter and a second circular polarizing filter, wherein the polarizing directions of the first and second circular polarizing filter are offset 90° from one another.

7. The assembly (100) according to claim 3, wherein the at least two polarization devices (31, 32) comprise a first circular polarizing filter and a second circular polarizing filter, wherein rotational direction of polarization of the first polarizing filter in the direction of the impinging beam of unpolarized light and rotational direction of polarization of the second polarizing filter in the direction of the impinging beam of unpolarized light is equal.

8. The assembly (100) according to claim 7, wherein the at least one optical detector (20a, 20b, 20c, 20d) is assigned to a linear polarizing filter (21a, 21b, 21c, 21d).

9. The assembly (100) according to claim 3, wherein the at least two polarization devices are spaced apart from one another in the direction of the beam of unpolarized light at a distance of less than 5 mm, preferably less than 2 mm.

10. The assembly (100) according to claim 1, wherein the absorption device (30) comprises at least two polarization devices (31, 32) arranged successively in the direction of the beam of unpolarized light.

11. The assembly (100) according to claim 10, wherein the at least two polarization devices are spaced apart from one another in the direction of the beam of unpolarized light at a distance of less than 5 mm, preferably less than 2 mm.

12. The assembly (100) according to claim 10, wherein the at least two polarization devices (31, 32) comprise a first linear polarizing filter and a second linear polarizing filter, wherein the polarizing directions of the first and second linear polarizing filter are offset 90° from one another.

13. The assembly (100) according to claim 10, wherein the at least two polarization devices (31, 32) comprise a first circular polarizing filter and a second circular polarizing filter, wherein the polarizing directions of the first and second circular polarizing filter are offset 90° from one another.

14. The assembly (100) according to claim 10, wherein the at least two polarization devices (31, 32) comprise a first circular polarizing filter and a second circular polarizing filter, wherein rotational direction of polarization of the first polarizing filter in the direction of the impinging beam of unpolarized light and rotational direction of polarization of the second polarizing filter in the direction of the impinging beam of unpolarized light is equal.

15. The assembly (100) according to claim 1, wherein the at least one polarization device (31, 32) is exchangeably accommodated in a retaining device (35) arranged downstream the useful light region in the direction of the beam of unpolarized light.

16. The assembly (100) according to claim 1, wherein the light source comprises a light-emitting diode (11) and preferably at least one lens (12) and preferably at least one aperture (13).

17. A scattered light smoke detector having at least one supply opening for supplying ambient air and the assembly in accordance with claim 1, wherein a feed opening empties into a scattered light region, and wherein at least part of the scattered light region corresponds to the useful light region.

* * * * *